(12) United States Patent
Palmer

(10) Patent No.: US 8,044,248 B2
(45) Date of Patent: Oct. 25, 2011

(54) TREATMENT OF BISPHENOL-A RESIDUE STREAMS

(75) Inventor: David P. Palmer, Katy, TX (US)

(73) Assignee: Badger Licensing LLC, Cambridge, MA (US)

( * ) Notice: Subject to any disclaimer, the term of this patent is extended or adjusted under 35 U.S.C. 154(b) by 239 days.

(21) Appl. No.: 12/396,725

(22) Filed: Mar. 3, 2009

(65) Prior Publication Data
US 2009/0249684 A1    Oct. 8, 2009

Related U.S. Application Data

(60) Provisional application No. 61/042,108, filed on Apr. 3, 2008.

(51) Int. Cl.
*C07C 37/88* (2006.01)
*C07C 39/16* (2006.01)

(52) U.S. Cl. .......................... 568/728; 568/724; 568/749

(58) Field of Classification Search .................. None
See application file for complete search history.

(56) References Cited

U.S. PATENT DOCUMENTS

| | | | |
|---|---|---|---|
| 3,466,337 A | | 9/1969 | Smith et al. |
| 4,131,749 A | | 12/1978 | Kiedik et al. |
| 4,180,683 A | * | 12/1979 | Mitchell ........................ 568/724 |
| 4,188,496 A | * | 2/1980 | Jaquiss et al. .................. 568/723 |
| 4,192,954 A | * | 3/1980 | Barker et al. .................. 568/723 |
| 4,327,229 A | * | 4/1982 | Mendiratta .................... 568/728 |
| 5,430,199 A | * | 7/1995 | Caruso et al. .................. 568/724 |
| 5,504,251 A | | 4/1996 | Dyckman et al. |
| 5,672,774 A | | 9/1997 | Dyckman et al. |
| 6,025,530 A | | 2/2000 | Dyckman et al. |
| 6,133,486 A | | 10/2000 | Maas et al. |
| 6,303,835 B1 | | 10/2001 | Shafer et al. |
| 6,459,004 B1 | | 10/2002 | Ono et al. |

FOREIGN PATENT DOCUMENTS
WO    2007044139    4/2007

OTHER PUBLICATIONS
Written Opinion of the International Searching Authority, mailed Aug. 28, 2009.
International Search Report, mailed Aug. 28, 2009.

* cited by examiner

*Primary Examiner* — Brian J Davis
(74) *Attorney, Agent, or Firm* — Roberts Mlotkowski Safran & Cole, P.C.

(57) ABSTRACT

In a method of reducing the viscosity of a residue stream from the production of bisphenol-A, the residue stream is combined with at least one of (a) a bottoms stream comprising polyalkylaromatic compounds and remaining after the fractionation of an effluent from an aromatics alkylation process to remove monoalkylaromatic compounds, (b) a stream containing at least 90 wt % phenol and (c) a mixture of phenol and said bottoms stream (a) to produce a combined stream.

25 Claims, 1 Drawing Sheet

US 8,044,248 B2

TREATMENT OF BISPHENOL-A RESIDUE STREAMS

PRIORITY CLAIM

This application claims the benefit of U.S. Provisional Application No. 61/042,108, filed Apr. 3, 2008, the entire contents of which are incorporated herein by reference.

FIELD

The present invention relates to treatment of bisphenol-A residue streams.

BACKGROUND

Bisphenol-A (4,4'-dihydroxy-2,2-diphenylpropane or BPA) is produced by condensation of acetone with an excess of phenol in the presence of an acidic catalyst or a cation-exchange resin. The crude product, in addition to the desired bisphenol-A and unreacted phenol, contains unwanted by-products, such as bisphenol-A isomers, trisphenol and other higher molecular weight materials. The bisphenol-A is normally separated from the crude product by a single or a series of crystallization steps, leaving a mother liquor stream enriched in unwanted by-products, a portion of which stream is removed to purge unwanted by-products from the process. Alternately, the bisphenol-A may be separated from the crude product by a single or series of distillation steps, which also creates a stream enriched in unwanted by-products, a portion of which is removed. The removed stream may contain unreacted phenol and bisphenol-A as well as the unwanted by-products. Phenol is typically recovered from the removed stream by distillation, normally vacuum distillation, to create a residue stream. However, the viscosity of the residue stream increases as the weight fraction of the phenol in the residue stream decreases, making handling of this residue stream increasingly difficult.

Additionally, the bisphenol-A isomers, trisphenol and higher molecular weight materials in the residue stream may be subjected to thermal or catalytic cracking to generate phenol and isopropenylphenol (IPP) for enhanced recovery. The cracking step may be subsequent to or coincident with phenol recovery by distillation. However, the cracking process also increases the viscosity of the remaining residue stream, a tarry aromatic waste material containing less than 5 wt %, typically less than 1 wt %, phenol. Because this material is highly viscous, it is difficult to handle by conventional means and normally must be maintained at a temperature above 130° C., preferably above 160° C., to ensure its flowability.

There is therefore interest in developing methods of reducing the viscosity of BPA residue streams so as to facilitate their transportation, use and disposal. One such method is disclosed in U.S. Pat. No. 5,504,251, which teaches that the viscosity of bisphenol-A residual tars can be reduced by combination with the tar remaining when cumene is converted to phenol by the Hock process. The phenol tar is said to comprise 10-25 wt % phenol, 10-25wt % acetophenone, 3-5wt % dimethylbenzylalcohol, 20-40 wt % o,p-cumylphenol, and 5-10 wt % alpha-methylstyrene dimer, with the remainder being heavy tar. Although the weight ratio of bisphenol-A tar to phenol tar may range from about 99:1 to about 1:99, optimum reduction in viscosity of the heavy bisphenol-A tar is said to be obtained when the ratio of bisphenol-A tar to phenol tar is in the range of 1:10 to 1:1. The mixture of bisphenol-A tar and phenol tar can be thermally decomposed at a temperature of about 290° C. to about 360° C. to yield phenol, alpha-methylstyrene and cumene.

Other examples of cracking of mixtures of bisphenol-A tar and phenol tar can be found in, for example, U.S. Pat. Nos. 5,672,774 and 6,025,530.

According to the present invention, it has now been found that the viscosity of a BPA residue stream can reduced by combining the stream with (a) the waste heavy ends stream from an alkylaromatic production process, composed mainly of polyalkylated aromatic compounds, (b) additional phenol or a mixture of (a) and (b). In general, however, excessive use of phenol alone as the viscosity reducing diluent is undesirable since phenol is generally a higher value product than both the BPA residue stream and the alkylaromatic waste stream. Irrespective of the diluent employed, the blended stream is suitable for use as a boiler fuel.

SUMMARY

In one aspect, the invention resides in a method of reducing the viscosity of a residue stream from the production of bisphenol-A, the method comprising combining the residue stream with at least one of (a) a bottoms stream comprising polyalkylaromatic compounds and remaining after the fractionation of an effluent from an aromatics alkylation process to remove monoalkylaromatic compounds, (b) a stream containing at least 90 wt % phenol and (c) a mixture of phenol and said bottoms stream (a) to produce a combined stream.

In one embodiment, the residue stream is combined with said bottoms stream (a) and said bottoms stream (a) comprises a mixture of polyalkylated benzenes, diphenylalkanes, and heavier aromatic compounds. Typically, the polyalkylated benzenes comprise polyethylbenzenes and/or polyisopropylbenzenes, especially polyisopropylbenzenes.

Conveniently, the weight ratio of said residue stream to said bottoms stream is between about 25:1 and about 4:1, such as between about 20:1 and about 9:1.

In a further embodiment, the residue stream is combined with a stream containing at least 90 wt % phenol such that the combined stream comprises between about 5 wt % and 15 wt % phenol.

In a further embodiment, the residue stream is combined with a mixture of phenol and said bottoms stream (a).

Conveniently, the combined stream is further combined with phenol tar.

Conveniently, said residue stream comprises less than 20 wt %, for example 10 wt %, such as less than 5 wt %, even less than 1 wt %, phenol.

In one embodiment, said residue stream comprises from about 2 to about 50 wt % p,p-BPA isomer, from about 1 to about 25 wt % o,p-BPA isomer, from about 1 to about 15 wt % trisphenol, and from about 15 to about 95 wt % BPA heavies comprising isopropenyl phenol dimers, hydroxyphenyl chromans, indanes and other heavier aromatic compounds In a further aspect, the invention resides in a method of producing bisphenol-A, the method comprising:

(a) condensing acetone with a molar excess of phenol in the presence of a catalyst under conditions to produce a product stream comprising bisphenol-A isomers, unreacted phenol, trisphenols, hydroxyphenyl chromans, isopropenyl phenol dimers, and indanes;

(b) recovering bisphenol-A and unreacted phenol from said effluent stream to leave a residue stream comprising bisphenol-A isomers, unrecovered phenol, trisphenols, hydroxyphenyl chromans, isopropenyl phenol dimers, indanes and other heavier aromatic compounds; and (c) combining at least part of the residue stream with at least one of (a) a bottoms stream comprising polyalkylaromatic compounds and remaining after the fractionation of an effluent from an aromatics alkylation process to remove monoalkylaromatic compounds, (b) a stream containing at least 90 wt % phenol and (c) a mixture of phenol and said bottoms stream (a) to produce a combined stream.

Conveniently, said effluent stream is cracked to convert and remove part of the effluent stream as isopropenyl phenol and/or phenol prior to said combining (c).

Conveniently, said bottoms stream is produced by an aromatics alkylation process comprising:

(d) contacting benzene with an alkylating agent having 2 to 5 carbon atoms in the presence of a catalyst and under conditions to form an alkylation effluent stream comprising monoalkylbenzene, dialkylbenzenes and trialkylbenzenes; and (e) removing monoalkylbenzene and dialkylbenzenes by distillation from said effluent stream to leave said bottoms stream comprising said trialkylbenzenes.

In one embodiment, said alkylating agent is ethylene and/or propylene.

DETAILED DESCRIPTION OF THE EMBODIMENTS

Figure 1:
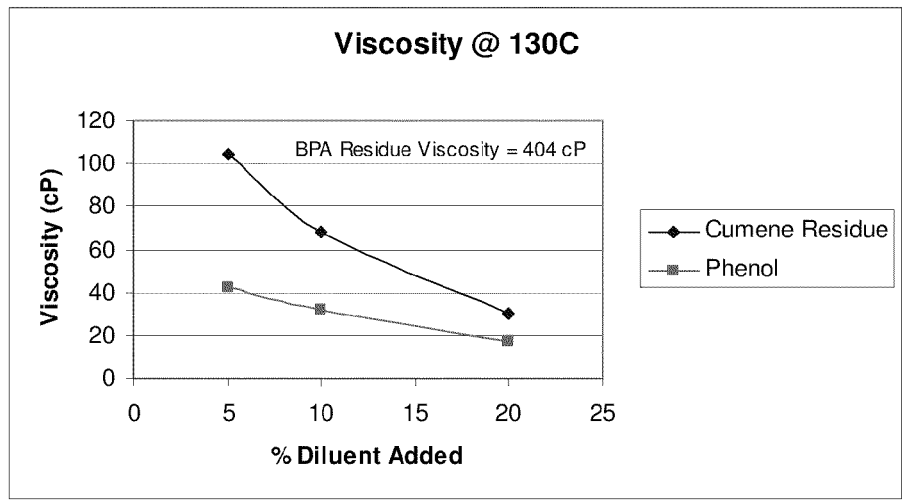
FIG. 1 is a graph of viscosity at 130° C. against wt % diluent added for a BPA residue stream diluted with a cumene residue stream according to the process of Example 2 or with phenol according to the process of Example 3.

The present invention is directed to a method of producing bisphenol-A (BPA), in which the viscosity of the residue remaining after recovery of the BPA product is reduced by combining the residue with the bottoms stream from an aromatics alkylation process and/or a phenol stream. The combined stream is a miscible liquid with significantly reduced viscosity as compared with the untreated BPA residue stream. As a result, the combined stream can be handled using a conventional centrifugal pump and can be stored without loss of flowability at a temperature 130° C. as compared with the storage temperature of 160° C. normally required for BPA residue streams. The combined stream is suitable for use as a liquid fuel for a steam generator.

The bisphenol-A (BPA) synthesis method initially involves reacting acetone with stoichiometrically excess phenol in the presence of an acid catalyst. The phenol/acetone molar ratio is usually in the range from 3 to 30, typically from 5 to 20. The reaction is carried out at a temperature of usually from 50 to 100° C. under a pressure of usually from atmospheric pressure to 600 kPa.

As the catalyst, usually strong mineral acids or strongly acidic cation exchange resins such as sulfonic acid type resins, including those partially neutralized with a sulfur-containing amine compound are used. As the sulfur-containing amine compound, ordinary promoters used for the synthesis of bisphenol A such as, for example, 2-(4-pyridyl) ethanethiol, 2-mercaptoethylamine, 3-mercaptopropylamine, N,N-dimethyl-3-mercaptopropylamine, N,N-di-n-butyl-4-mercaptobutylamine, and 2,2-dimethylthiazolidine can be used. Such a promoter is used in an amount of usually 2 to 30 mol %, such as 5 to 20 mol % based on the acid group (sulfonic group) in the acid ion exchanger.

The condensation reaction of the phenol and acetone is typically conducted in a fixed bed continuous flow system or a suspended bed batch system. In the case of the fixed bed flow system, the liquid space velocity of the mixture of the raw materials supplied to the reactor is usually 0.2 to 50 hr$^{-1}$. In the case of the suspended bed batch system, the amount of the strongly acid ion exchange resin used, although variable depending on the reaction temperature and pressure, is usually 20 to 100% by weight based on the mixture of the raw materials. The reaction time is usually 0.5 to 5 hours.

In addition to the desired bisphenol-A, the effluent from the condensation reaction comprises reaction-generated water, unreacted acetone, unreacted phenol, and a variety unwanted by-products, such as bisphenol-A isomers (for example, 2-(4-hydroxyphenyl)-2-(2-hydroxyphenyl)propane or o,p-BPA), trisphenol (see formula I below), isopropenyl phenol (IPP) dimers (see formulae Ia, IIb and IIc below) and hydroxyphenyl chromans (see formulae IIIa and IIIb below), substituted xanthenes and more highly condensed compounds having three or more phenyl rings in the molecular framework. Collectively, the IPP dimers, hydroxylphenyl chromans, indanes, xanthenes and more highly condensed compounds are termed as "BPA heavies."

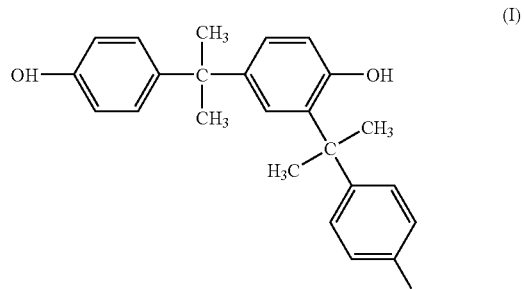

(I)

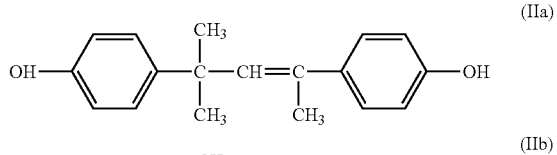

(IIa)

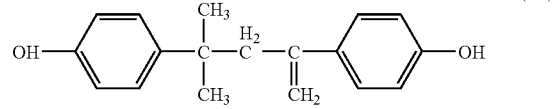

(IIb)

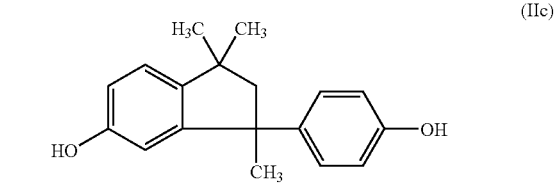

(IIc)

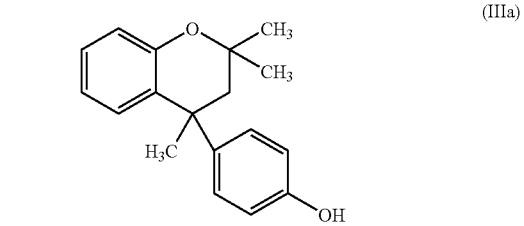

(IIIa)

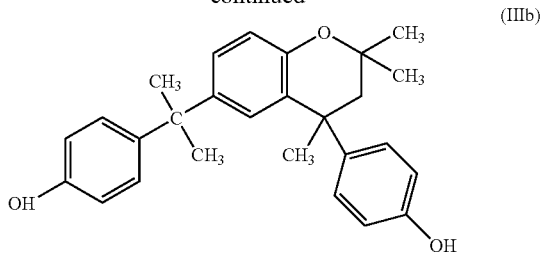

(IIIb)

These by-products, as well as the water, phenol and acetone, impair the suitability of the BPA for the production of polymers and must be separated from the condensation effluent. For the production of polycarbonate in particular, high demands are made on the purity of the raw material BPA.

The purification of the BPA is carried out by a multi-stage cascade of suitable purification processes such as, for example, suspension crystallization, melt crystallization, distillation and/or desorption. After separation of the BPA product, these processes leave a mother liquor which contains BPA, water, unreacted phenol and possibly unreacted acetone, and which is rich in the above-mentioned by-products. Typically, this stream of mother liquor is recycled to the condensation reaction. In order to maintain the catalytic activity of the acidic ion exchanger, all or some of the water that has formed is removed beforehand by distillation, together with any unreacted acetone that is still present. The dewatered mother liquor so obtained is supplemented with additional phenol and acetone and fed back into the condensation unit.

Such a recycle procedure has the disadvantage that the by-products of the BPA preparation become concentrated in the circulating stream and can adversely affect the purity of the final BPA product and may lead to deactivation of the catalyst system. In order to avoid excessive concentration of the by-products in the circulating stream, a portion of the mother liquor mixture must be discharged from the system. The discharge is typically effected by removing a portion of the mother liquor from the circulating stream, often after distillation to remove water of reaction, unreacted acetone and part of the unreacted phenol. The composition of the mother liquor at this point, and accordingly also the composition of the discharge, typically comprises from 60 to 90 wt. % phenol, from 6 to 18 wt. % BPA and from 3 to 15 wt. % BPA isomers and heavier by-products. Since this discharge stream contains significant quantities of phenol and other useful products, the discharge is a valuable process stream which is subjected to further processing.

In one embodiment, further processing of the discharge stream involves distilling off the phenol to a residual content of less than 20 wt %, such as less than 10 wt. %, especially less than 5 wt. %, even less than 1 wt. %, normally by vacuum distillation, leaving a heavy residue stream comprising <10 wt. % phenol, from 15 to 85 wt. % BPA and from 15 to 85 wt. % by-products, which residue stream must be removed from the process and disposed of, for example, by burning or dumping.

In another embodiment, further processing of the discharge stream involves subjecting the bisphenol-A isomers, trisphenols and other high molecular weight components in the discharge stream to thermal or catalytic cracking to generate phenol and isopropenylphenol (IPP) for enhanced recovery. The cracking step may be subsequent to or coincident with phenol recovery by distillation. A suitable cracking process is described in International Patent Publication No. WO 2007/044139, the entire contents of which are incorporated herein by reference. Again the cracking step leaves a heavy residue stream comprising <10 wt. %, especially <5 wt. %, even <1 wt. % phenol, from 2 to 20 wt. % BPA and from 70 to 95 wt. % by-products, which residue stream must be removed from the process and disposed of, for example, by burning or dumping.

Irrespective of whether further processing of the discharge stream involves distillation or cracking or both, as the lighter products, particularly phenol, are removed from the stream, its viscosity increases making it increasingly difficult to transport and handle. The present process provides a method of reducing the viscosity of the heavy residue streams produced in the production of BPA and in particular of those BPA heavy residue streams having the compositions listed in the following table:

|  | Broad | Uncracked Residue | Cracked Residue |
| --- | --- | --- | --- |
| Phenol | <20 wt % | 0 to 10 wt % | 0 to 5 wt % |
| p,p-bisphenol-A (BPA) | 2 to 50 wt % | 30 to 50 wt % | 2 to 20 wt % |
| o,p-bisphenol-A | 1 to 25 wt % | 10 to 25 wt % | 1 to 10 wt % |
| Trisphenol | 1 to 15 wt % | 2 to 10 wt % | 1 to 15 wt % |
| Heavies | 15 to 95 wt % | 15 to 35 wt % | 60 to 95 wt % |

The viscosity reducing process comprises combining the BPA heavy residue stream with at least one of (a) the bottoms stream remaining after the fractionation of the effluent from an aromatics alkylation process to remove at least the monoalkylaromatic compounds, (b) a stream containing at least 90 wt % phenol and (c) a mixture of phenol and said bottoms stream (a).

In connection with the bottoms stream (a), in a conventional aromatics alkylation process for producing a monoalkylated product, depending on the conditions and catalyst employed, the alkylation effluent will contain dialkylated, trialkylated and possibly even higher alkylated species as well other impurities, such as diphenylalkanes. Moreover, although the dialkylated species can normally be separated from the monoalkylated species and subjected to transalkylation to produce additional monoalkylated product, the higher alkylated species are not normally amenable to transalkylation and are discarded. It has now been found that these polyalkylaromatic-containing residue streams are miscible with BPA residue streams and are effective in reducing the viscosity of such BPA residue streams.

Suitable polyalkylaromatic-containing residue streams are residue streams containing polyalkylated benzenes, especially dialkylbenzenes and trialkylbenzenes, diphenylalkanes, and heavier aromatic compounds. Particularly suitable are the polyalkylbenzene residue streams generated by the alkylation of benzene with ethylene and/or propylene. Most preferred are cumene residue streams since cumene plants are often co-located with BPA plants.

Generally the weight ratio of the BPA residue stream to the aromatics alkylation bottoms stream is between about 25:1 and about 4:1, such as between about 20:1 and about 9:1.

Similarly, it is found that streams containing at least 90 wt % phenol, such as 99 wt % and even pure phenol, both alone and in combination with polyalkylaromatic-containing residue streams, are effective in lowering the viscosity of BPA residue streams, even where the total content of the combined phenol/BPA stream is only about 5 wt % to about 15 wt %.

In addition to the polyalkylaromatic-containing residue streams and/or the phenol-containing stream, the BPA residue stream can be combined with a phenol tar stream.

Combining the BPA residue stream with the diluent streams described herein can be effected by any conventional means, such as a mechanical agitator, a static mixer or a pump impeller. The combined stream is generally arranged to have a viscosity at 130° C. of less than 150 cP and a viscosity at 160° C. of less than 25 cP. The combined stream is suitable for use as a boiler fuel.

The invention will now be more particularly described with reference to the Examples and the accompanying drawings.

All viscosity measurements in the Examples were made using a Brookfield Model LVT Viscometer.

Example 1

A BPA residue was produced by catalytically cracking the mother liquor remaining after subjecting the effluent from the condensation of phenol and acetone to multiple crystallization steps to remove the BPA product. The cracking was conducted at the following conditions: 230° C., 130 mmHg, 200 ppm caustic, and about 3.5 hours residence time. Four separate batches of residue each weighing about 450 grams were produced. The composition of the combined batches of cracked residue was about 20 wt % p,p-BPA isomer, 10 wt % trisphenol, 5 wt % o,p-BPA isomer, and 4 wt % phenol, with the balance of the residue consisted of BPA heavies (IPP dimers, hydroxyphenyl-chromans, indanes and other higher molecular weight aromatic compounds).

To establish a baseline, the BPA residue viscosity without any added phenol or cumene residue was measured at several temperatures. At a temperature of 96.8° C., the viscosity reading was off the scale of the instrument. At 120° C., the viscosity of the BPA residue was around 950 cP. At about 130° C., the average viscosity was measured to be 404 cP. Finally, at 160° C., the average viscosity was 52 cP.

A bottoms stream comprising polyalkylbenzene compounds, and remaining after the fractionation of di-isopropyl benzenes obtained from a commercial cumene manufacturing facility, had the following composition: 5 wt % triisopropylbenzenes, 7 wt % heavier than triisopropylbenzenes and lighter than tetraisopropylbenzenes, 28 wt % tetraisopropylbenzene and higher polyalkylated benzenes, 18 wt % diphenylpropane, and 42 wt % diphenylpropane.

The average viscosity of the cumene residue was 9.1 cP at a temperature of 21.5° C.

Two experiments were performed to determine whether the BPA and cumene residues were miscible. In a first experiment, 20.2 grams of BPA residue and 5.2 grams of cumene residue were added to a 50 ml flat bottom flask set in a 250 ml beaker oil bath. A thermocouple was installed in the flask to measure the temperature as well as provide a means for mixing the residues. The flask was heated to 160° C. and the flask removed to observe the contents. At this point all the contents were melted and well-mixed. Upon cooling, no phase separation was observed.

In a second experiment, 20.0 grams of the BPA residue was charged to the flask and heated to 99° C. At this temperature, the BPA residue was still tar-like. 5.0 grams of cumene residue were then added to the flask and mixed. The resulting mixture showed a single phase and was very fluid.

Example 2

Figure 2:
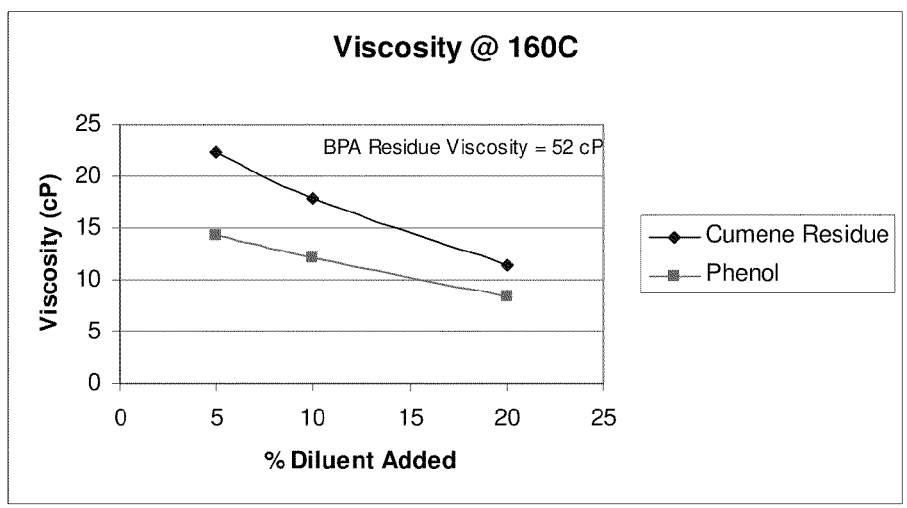
FIG. 2 is a graph of viscosity at 160° C. against wt % diluent added for a BPA residue stream diluted with a cumene residue stream according to the process of Example 2 or with phenol according to the process of Example 3.

After showing that the BPA and cumene residues were miscible, experiments were performed to measure the viscosity of various mixtures of the BPA residue with the cumene residue. Initially the BPA residue produced from the cracking unit was mixed with 5 wt % of the cumene residue. The viscosity for the mixture was measured at two temperatures, 130° C. and 160° C. Additional cumene residue was then added to bring the dilution to 10% and the viscosity measured. Finally, more cumene residue was added to bring the dilution to 20% and the viscosity measured. The results are shown in Table 1 and FIGS. 1 and 2.

Example 3

The process of Example 2 was repeated but with pure phenol being used as the diluent. Again, the results are shown in Table 1 and FIGS. 1 and 2.

Example 4

An additional experiment was performed where the BPA residue was mixed with 5 wt % phenol and 5 wt % cumene residue. The results are presented in Table 1. Surprisingly, dilution with a mixture of phenol and cumene resulted in a lower viscosity than equivalent weight fraction of phenol or cumene residue alone.

TABLE 1

| Percent BPA Residue | Percent Cumene Residue | Percent Phenol | T = 130° C. Viscosity cP | T = 160° C. Viscosity cP |
|---|---|---|---|---|
| 100 | 0 | 0 | 404 | 52 |
| 95 | 5 | 0 | 104 | 22 |
| 90 | 10 | 0 | 68 | 18 |
| 80 | 20 | 0 | 30 | 12 |
| 95 | 0 | 5 | 42 | 14 |
| 90 | 0 | 10 | 32 | 12 |
| 80 | 0 | 20 | 17 | 8 |
| 90 | 5 | 5 | 23 | 10 |

While the present invention has been described and illustrated by reference to particular embodiments, those of ordinary skill in the art will appreciate that the invention lends itself to variations not necessarily illustrated herein. For this reason, then, reference should be made solely to the appended claims for purposes of determining the true scope of the present invention.

The invention claimed is:

1. A method of reducing the viscosity of a residue stream from the production of bisphenol-A, the method comprising combining the residue stream with a bottoms stream (a) comprising polyalkylaromatic compounds remaining after the fractionation of an effluent from an aromatics alkylation process to remove monoalkylaromatic compounds, and optionally a stream (b) containing at least 90 wt % phenol to produce a combined stream.

2. The method of claim 1, wherein said bottoms stream (a) comprises a mixture of polyalkylated benzenes, diphenylalkanes, and heavier aromatic compounds.

3. The method of claim 2, wherein the polyalkylated benzenes of said bottoms stream comprise polyethylbenzenes and/or polyisopropylbenzenes.

4. The method of claim 2, wherein the polyalkylated benzenes of said bottoms stream comprise polyisopropylbenzenes.

5. The method of claim 2, wherein the weight ratio of said residue stream to said bottoms stream is between about 25:1 and about 4:1.

6. The method of claim 2, wherein the weight ratio of said residue stream to said bottoms stream is between about 20:1 and about 9:1.

7. The method of claim 1, wherein the residue stream is further combined with said optional stream (b) and the combined stream comprises between about 5 wt % and about 15 wt % phenol.

8. The method of claim 1, wherein the residue stream is combined with a mixture of phenol and said bottoms stream (a).

9. The method of claim 1, wherein the combined stream is further combined with phenol tar.

10. The method of claim 1, wherein said combined stream comprises less than 20 wt % phenol.

11. The method of claim 1, wherein said combined stream comprises less than 10 wt % phenol.

12. The method of claim 1, wherein said combined stream comprises less than 1 wt % phenol.

13. The method of claim 1, wherein said residue combined stream comprises from about 2 to about 50 wt % p,p-BPA isomer, from about 1 to about 25 wt % o,p-BPA isomer, from about 1 to about 15 wt % trisphenol, and from about 15 to about 95 wt % BPA heavies comprising isopropenyl phenol dimers, hydroxyphenyl chromans, indanes and other heavier aromatic compounds.

14. A method of producing bisphenol-A, the method comprising:
   (a) condensing acetone with a molar excess of phenol in the presence of a catalyst under conditions to produce a product stream comprising bisphenol-A isomers, unreacted phenol, trisphenols, hydroxyphenyl chromans, isopropenyl phenol dimers, and indanes;
   (b) recovering bisphenol-A and unreacted phenol from said effluent stream to leave a residue stream comprising bisphenol-A isomers, unrecovered phenol, trisphenols, hydroxyphenyl chromans, isopropenyl phenol dimers, indanes and other heavier aromatic compounds; and
   (c) combining at least part of the residue stream with a bottoms stream (a) comprising polyalkylaromatic compounds remaining after the fractionation of an effluent from an aromatics alkylation process to remove monoalkylaromatic compounds, and optionally a stream (b) containing at least 90 wt % phenol to produce a combined stream.

15. The method of claim 14, wherein said effluent stream is cracked to convert and remove part of the effluent stream as isopropenyl phenol and/or phenol prior to said combining.

16. The method of claim 14, wherein said combined stream comprises less than 5 wt % phenol.

17. The method of claim 14, wherein said combined stream comprises less than 1 wt % phenol.

18. The method of claim 14, wherein said combined stream comprises from about 2 to about 50 wt % p,p-BPA isomer, from about 1 to about 25 wt % o,p-BPA isomer, from about 1 to about 15 wt % trisphenol, and from about 15 to about 95 wt % BPA heavies comprising isopropenyl phenol dimers, hydroxyphenyl chromans, indanes and other heavier aromatic compounds.

19. The method of claim 14, wherein said bottoms stream (a) is produced by an aromatics alkylation process comprising:
   (d) contacting benzene with an alkylating agent having 2 to 5 carbon atoms in the presence of a catalyst and under conditions to form an alkylation effluent stream comprising monoalkylbenzene, dialkylbenzenes and trialkylbenzenes; and
   (e) removing monoalkylbenzene and dialkylbenzenes by distillation from said effluent stream to leave said bottoms stream (a) comprising said trialkylbenzenes.

20. The method of claim 19, wherein said alkylating agent comprises ethylene.

21. The method of claim 19, wherein said alkylating agent comprises propylene.

22. The method of claim 19, wherein the weight ratio of said residue stream to said bottoms stream is between about 25:1 and about 4:1.

23. The method of claim 14, wherein the residue stream is further combined with said optional stream (b) and the combined stream comprises between about 5 wt % and about 15 wt % phenol.

24. The method of claim 14, wherein the residue stream is combined with a mixture of phenol and said bottoms stream (a).

25. The method of claim 14, wherein the combined stream is further combined with phenol tar.

* * * * *